United States Patent [19]

Willis et al.

[11] Patent Number: 5,266,222

[45] Date of Patent: Nov. 30, 1993

[54] DURABLE LOW SURFACE-ENERGY SURFACES

[75] Inventors: Paul B. Willis, La Canada; Paul M. McElroy, La Crescenta; Gregory H. Hickey, Altadena, all of Calif.

[73] Assignee: California Institute of Technology, Pasadena, Calif.

[21] Appl. No.: 847,384

[22] Filed: Mar. 6, 1992

Related U.S. Application Data

[63] Continuation-in-part of Ser. No. 527,617, May 23, 1990, abandoned.

[51] Int. Cl.[5] .......................................... C10M 139/04
[52] U.S. Cl. .................................... 252/49.006; 106/2; 106/38.22; 106/287.11; 106/287.13; 523/169
[58] Field of Search ................... 252/49.6; 106/287.11, 106/287.13, 2, 38.22; 523/169

[56] References Cited

U.S. PATENT DOCUMENTS

| | | | |
|---|---|---|---|
| 3,803,050 | 4/1974 | Haas et al. | 252/408 |
| 3,989,354 | 11/1976 | Dubois et al. | 350/160 LC |
| 4,277,525 | 7/1981 | Nakayama et al. | 427/387 |
| 4,316,041 | 2/1982 | Totten et al. | 556/420 |
| 4,358,391 | 11/1982 | Finkelmann et al. | 252/299.01 |
| 4,388,453 | 6/1983 | Finkelmann et al. | 528/15 |
| 4,548,842 | 10/1985 | Pohl | 427/407.2 |
| 4,678,283 | 7/1987 | Kreuzer et al. | 350/340 |
| 4,730,904 | 3/1988 | Pauluth et al. | 350/340 |
| 4,990,377 | 2/1991 | Wilson | 106/287.13 |

FOREIGN PATENT DOCUMENTS

| | | | |
|---|---|---|---|
| 51-1387 | 1/1976 | Japan . | |
| 511387 | 1/1976 | Japan | 106/287.13 |
| 746306 | 3/1956 | United Kingdom | 106/287.13 |

*Primary Examiner*—Jacqueline V. Howard
*Attorney, Agent, or Firm*—F. Eugene Logan

[57] ABSTRACT

A formulation for forming a low surface-energy surface on a substrate having (i) a fluoroalkyl silane having a low surface energy part, (ii) a liquid crystal silane operable for enhancing the orientation of the molecules of the fluoroalkyl silane and for crosslinking with the fluoroalkyl silane, and, (iii) a transport medium for applying the fluoroalkyl silane and the liquid crystal silane to the surface of a substrate. In one embodiment the formulation can includes a crosslinking agent for crosslinking the fluoroalkyl silane. In another embodiment the formulation has a condensation catalyst for enhancing chemical bonding of the fluoroalkyl silane to the substrate. The transport medium can be an alcohol such as methanol or ethanol.

30 Claims, 1 Drawing Sheet

DURABLE LOW SURFACE-ENERGY SURFACES

ORIGIN OF INVENTION

The invention described herein was made in the performance of work under a NASA contract, and is subject to the provisions of Public Law 96-517 (35 USC 202) in which the Contractor has elected to retain title.

RELATED U.S. APPLICATION

Continuation-in-part of Ser. No. 527,617 filed May 23, 1990 now abandoned.

BACKGROUND OF THE INVENTION

1. Technical Field

This invention is directed towards low surface-energy surfaces, methods of producing low surface-energy surfaces on various substrates, and, formulations for treating surfaces to produce low surface-energy surfaces.

2. Background Art

Fluorinated hydrocarbons such as polytetrafluorethylenes have been used to form coatings on surfaces which resist acids and organic solvents. Liquid crystals have been used for electrooptical displays, passivating agents, doped oxides, protective films on metals, antistatic coatings and for other purposes as represented generally by the following patents. It is not believed that liquid crystal silanes in combination with fluoroalkyl silanes have been used to produce improved non-wettable or low surface-energy surfaces.

U.S. Pat. No. 4,730,904 to Pauluth et al discloses a group of organosilicon compounds which are said to have better, more uniform and more stable, homotropic orientation of liquid crystal on glass surfaces. These compounds are used for electrooptical display elements.

U.S. Pat. No. 4,277,525 to Nakayama et al disclose a silica-based liquid for coating glass. The liquid is obtained by the reaction of an alkoxysilane, a lower carboxylic acid and an alcohol, such as methanol, in the presence of an organic acid reaction accelerator. The coating are said to have excellent abrasion and chemical resistance and can be applied to glass plates as a passivating agent for providing passivation films on such surfaces, as a doped oxide on film on semiconductors, as protective films on metals, and as antistatic coating films on substrates.

U.S. Pat. No. 4,316,041 to Totten et al discloses certain liquid silanes, and more particularly certain alkoxy-, chloro-, and dimethyl amino silyl substituted compounds having liquid crystalline behavior, which can be chemically bonded to substrates, including glass, silica and other silicious materials, without the need for hermetic sealing. The chemical bonding of the silane to the substrate without the loss of its liquid crystal capability, is the primary objective of the invention.

U.S. Pat. No. 4,678,283 to Kreuzer et al discloses trialkanoyloxy silanes useful for generating a homeotropic orientation of liquid crystals on glass plate and ceramic surfaces used in visual electronic display elements.

U.S. Pat. No. 4,548,842 to Pohl discloses acylaminoorganosilicon compounds for treating glass surfaces to improve abrasion resistance, lubricity and durability to caustic wash compared to coatings containing organofunctionalsilane.

U.S. Pat. Nos. 4,388,453 and 4,358,391 to Finkelmann et al disclose crosslinked organopolysiloxanes having liquid crystal properties in which mesogenic molecules are chemically bonded to the organopolysiloxanes. The organopolysiloxanes are prepared from silanes or siloxanes containing mesogenic molecules which are crosslinked by addition or condensation reactions.

U.S. Pat. No. 3,803,050 to Haas et al discloses liquid crystal formulation which can be poured or sprayed onto a substrate, and, after evaporation of the solvent, a thin layer of liquid crystals is formed on the substrate. The substrate can be glass, ceramic or a variety of other materials.

U.S. Pat. No. 3,989,354 to Dubois et al discloses a nematic liquid crystal device having long-shaped molecules produced from hexamethyldisiloxane, and oriented perpendicular to electrodes plates for use in electrooptical displays.

Very few low surface energy treatments are available and those that are known all lack durability.

SUMMARY OF THE INVENTION

This invention is directed towards low surface-energy surfaces, methods of treatment of surfaces to obtain low surface energy, and formulations useful for producing low surface-energy surfaces. This invention treats surfaces with a fluoroalkyl silanes and liquid crystal silanes which enhance the orientation of the fluoroalkyl silanes on the surfaces so that a low surface-energy surfaces are produced. Good durability is achieved by chemically bonding of the molecules of the components to the surface of the treated substrate.

Surface free energy arises from an imbalance between the interior of a substance, where the intermolecular forces are satisfied among neighbor molecules, and, the exterior, where lack of neighbor molecules leaves residual unsatisfied forces remaining at the surface. The surface free energy is generally designated by the Greek letter gamma and measured in $mJ/m^2$ or equivalently $ergs/cm^2$. The drawing together of molecules at the surface produces an apparent tensile force, or "surface tension", which is also generally designated by the Greek letter gamma and measured in $mN/m$, or equivalently $dynes/cm$. Since the terms surface energy and surface tension are numerically identical, they are generally used interchangeably.

In particular, this invention is directed to a surface treatment for altering the surface energy of substrates by forming low surface-energy surfaces on various substrates which have good durability and excellent adhesion to the substrates.

Accordingly there is provided by the principles of this invention a formulation for forming a low surface-energy surface on a substrate comprising a fluoroalkyl silane having a low surface energy part; a liquid crystal silane for operable enhancing the orientation of the molecules of the fluoroalkyl silane and for crosslinking with the fluoroalkyl silane; and, a transport medium for applying the fluoroalkyl silane and the liquid crystal silane to the surface of a substrate. The molecules of the fluoroalkyl silane have a low energy part, i.e. the fluorinated part, and a substrate-chemically reactive part. An effective amount of the liquid crystal silane is used for enhancing the orientation of the molecules of the fluoroalkyl silane so that the low energy part thereof forms a surface on the substrate having a lower surface energy than such surface would have in the absence of the liquid crystal silane.

The fluoroalkyl silanes useful in this invention are linear-like with the non-fluorinated part forming one end of the molecules and the fluorinated part forming the other ends. The fluorinated part of the fluoroalkyl silanes provides low surface energy sites. We have found that certain liquid crystals have a synergistic effect when mixed with the fluoroalkyl silanes by orienting and aligning the fluoroalkyl silane molecules so that the fluorinated parts thereof are grouped together in a first group and the non-fluorinated parts thereof are grouped together in a second group. The fluorinated parts so oriented and aligned form a low energy surface. Not all liquid crystals are useful for producing such a synergistic effect. In particular we have found that the liquid crystal silanes which will crosslink with the fluoroalkyl silanes are operable for improving the low energy surfaces formed by fluoroalkyl silanes. Furthermore the nature of the crosslinking must be to improve the grouping of the fluorinated parts of the fluoroalkyl silane molecules so that an improved low energy surface is formed. The low surface energy surface is formed by virtue of the oriented fluoroalkyl silane molecules having their fluorinated parts aligned. Without the liquid crystal silane the surface energy resulting from the fluoroalkyl silane is higher than that achieved in the presence of the liquid crystal silanes.

In one embodiment of this invention the fluoroalkyl silane has the general formula

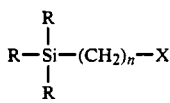

wherein "n" is at least 2, wherein at least one "R", which for ease of referral will be referred to as "R¹", is selected from the group consisting of alkyl groups, wherein at least one "R", which for ease of referral will be referred to as "R²", is selected from the group consisting of halogens, alkyl ethers, and mixtures thereof, which are hydrolyzable to form a silanol, and, wherein "X" is selected from the group consisting of fluorinated aliphatic groups, fluorinated alicyclic groups, and mixtures thereof, having a low surface energy part. One "R", which for ease of referral will be referred to as, "R³" can be any group which is non-deleterious to the formation of a low surface-energy surfaces. Alternatively R³ can be either R¹ or R². In one embodiment R³ is a member of R². In a still further embodiment R¹ is selected from the group consisting of methyl groups, ethyl groups, and mixtures thereof. In yet another embodiment R² is selected from the group consisting of Cl, Br, OCH₃, and OC₂H₅ radicals, and mixtures thereof, which are hydrolyzable to form a silanol. In one embodiment of this invention X is completely fluorinated. In another embodiment X is partially fluorinated. In still another embodiment the "n" is 2. In an especially preferred embodiment the fluoroalkyl silane is tridecafluoro-1,1,2,2-tetrahydrooctyl-1-triethoxysilane. Other non-limiting examples of fluoroalkyl silanes are: (Heptadecafluoro-1,1,2,2-tetrahydrodeccyl)-1-triethoxysilane; (Heptafluoroisopropoxy)propylmethyldichlorosilane; (Perfluoroisobutyl)trimethoxysilane; (Tridecafluoro-1,1,2,2-tetrahydrooctyl)-1-methyldichlorosilane; 1,1,2,2-Tetrahydroperfluoroundecyl-1-trimethoxysilane; Octafluorocyclopentyl-1-ethyltrimethoxysilane; (1-Trimethoxysilyl)-perfluorobutylpropionate; 1H,1H,2H,2H-Perfluorodecyltriethoxysilane; 1H,1H,2H,2H-Perfluorodecyltrichlorosilane; 1H,1H,2H,2H-Perfluorodecyldimethylchlorosilane; (1-Triethoxy)-1H,2H,2H-perfluorodecane; 1H,1H,2H,2H-Perfluorooctyltriethoxysilane; 1H,1H,2H,2H-Perfluorooctylmethyldichlorosilane; (Perfluoroheptylmethoxy)propyltrimethoxysilane; and (Tridecafluoro-1,1,2,2-tetrahydrooctyl)-1-trichlorosilane.

In one embodiment the second component of this invention, the liquid crystal silane, has the general formula

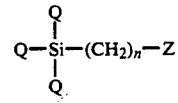

wherein "n" is at least 2, wherein "Q" is selected from the group consisting of halogens, alkyl ethers, and mixtures thereof, which are hydrolyzable to form a silanol, and, wherein "Z" is selected from the group consisting of organic groups having liquid crystal properties. It should be noted that for an "n" of 1 an unstable compound is formed. In one embodiment "n" is 3. All of the commercially available liquid crystal silanes, which are few in number, have propyl groups, i.e. n is 3. In another embodiment Q is selected from the group consisting of Cl, Br, OCH₃, OC₂H₅ radicals, and mixtures thereof, which are hydrolyzable to form a silanol. In a still further embodiment Z is selected from the group consisting of alkyl quaternary ammonium salts, substituted biphenyl compounds, terphenyl compounds, azoxybenezenes, cinnamates, pyrimidines, benzoates, and mixtures thereof. In an especially preferred embodiment the liquid crystal silane is n-octadecyldimethyl[3-(trimethoxysily)-propyl] ammonium chloride. Other non-limiting examples of liquid crystal silanes are: N-Octadecylaminopropyltrimethoxysilane; 3-Cyanopropyltrichlorosilane; Diisobutylsilanediol; N-Methylaminopropyltrimethoxysilane; Methyl-n-octadecyldichlorosilane; and (R)-N-a-Phenethyl-N-triethoxysilylpropyl-urea.

In another embodiment of this invention the formulation further comprises a crosslinking agent for enhancing the crosslinking of the fluoroalkyl silane. An effective amount of the crosslinking agent is used for crosslinking and orienting molecules of the fluoroalkyl silane so that the low energy part thereof forms a surface on the substrate having a lower surface energy than such surface would have in the absence of the crosslinking agent. In one embodiment the crosslinking agent is selected from the group consisting of multifunctional silyl ethers, multifunctional silicates, and mixtures thereof, which are capable of hydrolysis and reaction with the fluoroalkyl silane and the liquid crystal silane. In yet another embodiment the crosslinking agent is selected from the group consisting of tetramethyl orthosilicates, tetraethyl orthosilicates, and mixtures thereof. In an especially preferred embodiment the crosslinking agent is bis-1,2-(trimethoxysilyl)-ethane. Other non-limiting examples of crosslinking agents are: Dimethyldichlorosilane; Diethoxydichlorosilane; Tetrapropylorthosilicate; Tetrabutylorthosilicate; Bis-1,2-(Trichlorosilyl)ethane; 1,3-Bis(trimethoxysilyl)tetramethyldisiloxane; 1,4-Bis(hydrodimethylsilyl)benzene; Bis(2-trimethoxysilyl)-3-aminopropyltriethoxysilane; Diethyldiethoxysilane; 1,6-Bis(trichlorosilyl)-octane; Dimethyldimethoxysilane; Di-n-propyldichlorosilane;

Bis[3-(triethoxysilyl)propyl]-amine; Dimethyldiethoxysilane; Methyltrimethoxysilane; and Bis-(trimethoxysilylethyl)-benzene.

In still another embodiment of this invention the formulation further comprising a condensation catalyst for enhancing chemical bonding of the fluoroalkyl silane to the substrate. An effective amount of the condensation catalyst is used for enhancing the reaction of the substrate-chemically reactive part of the fluoroalkyl silane to the substrate surface so that the durability of the low surface-energy surface on the substrate is greater than the durability of such low surface-energy surface formed in the absence of the condensation catalyst. In one embodiment the condensation catalyst is selected from the group consisting of tertiary amines, hindered secondary amines, and mixtures thereof, which are capable of catalyzing the hydrolysis and condensation of the fluoroalkyl silane and the liquid crystal silane. By the term "hindered" as used herein is meant the presence of any chemical group, frequently methyl, that shields the hydrogen of a secondary amine nitrogen atom, and reduces its base strength. In a preferred embodiment the condensation catalyst is N,N-dimethyl benzylamine. Other non-limiting examples of condensation catalysts are: N-methylmorpholine; 2,2,6,6-Dimethylpiperazine; N,N-Dimethylpiperazine; triethylamine; Diphenylurea; Phenyldimethylamine; Tetramethylguanidine; 1,4-Diazo[2.2.2.]bicyclooctane; and 2-Aminoethyl-N-aminopropyltrimethoxysilane.

In one embodiment of this invention the fluoroalkyl silane and the liquid crystal silane are dissolved in the transport medium. In another embodiment the transport medium is an alcohol. In a further embodiment the alcohol is selected from the group consisting of methanol, ethanol, and mixtures thereof. In a preferred embodiment the alcohol is methanol.

In one embodiment of this invention the amount of fluoroalkyl silane is from about 0.4 to about 10% by weight of the formulation, and the amount of liquid crystal silane is from about 0.1 to about 5% by weight of the formulation. In another embodiment the amount of crosslinking agent is from about 0.1 to about 5% by weight of the formulation. In still another embodiment the amount of condensation catalyst is from about 0.05 to about 1% by weight of the formulation.

In yet another embodiment of this invention the weight ratio of the liquid crystal silane to the fluoroalkyl silane is from about 0.05 to about 0.5. In a further embodiment the weight ratio of the crosslinking agent to the fluoroalkyl silane is from about 0.05 to about 0.5. In another further embodiment the weight ratio of the condensation catalyst to the fluoroalkyl silane is from about 0.05 to about 0.25.

There is also provided by the principles of this invention a method of transforming a substrate surface into a low surface-energy surface comprising contacting the substrate surface with any of the above-mentioned low surface energy producing formulations; and, removing the transport medium from the formulation while it is in contact with the substrate surface, thereby transforming the substrate surface into a low surface-energy surface. In one embodiment of this invention where the transport medium is an alcohol, the alcohol, is removed by evaporation. If the formulation also contains a condensation catalyst, then in one embodiment the method further comprises removing the condensation catalyst by evaporation simultaneously with the removal of the alcohol.

There is also provided by the principals of this invention a substrate having a low surface-energy surface comprising a substrate having an original substrate surface; a fluoroalkyl silane having a molecular structure with a low energy part and a substrate-chemically reactive part; a chemical bond bonding the substrate-chemically reactive part to the original substrate surface; and, a liquid crystal silane enhancing the orientation of the fluoroalkyl silane so that the substrate-chemically reactive part of the fluoroalkyl silane is nearest to the original surface of the substrate and the low energy part extends outwardly therefrom. In one embodiment of this invention the substrates having low surface-energy surfaces further comprise a crosslinking agent enhancing the crosslinking and orientation of the molecules of fluoroalkyl silane on the surfaces of the substrates. In still another embodiment of this invention the chemical bonds bonding the substrate-chemically reactive part to the original surface of the substrates are formed in the presence of a condensation catalyst which enhances the chemical bonds. In one embodiment the original substrate surface comprises chemically bound hydroxyl groups. In another embodiment the original substrate surface is selected from the group consisting of glass, ceramics, and metals having chemically bound hydroxyl groups.

There is also provided by the principals of this invention a low surface-energy surface comprising crosslinked and oriented molecules of fluoroalkyl silane having a molecular structure with a low energy part and a substrate-chemically reactive part, wherein the low energy part of the molecules of fluoroalkyl silane form the low surface-energy surface; and, a chemical bond bonding the substrate-chemically reactive part to an original surface of a substrate. The liquid crystal silane enhances the orientation the fluoroalkyl silane so that the substrate-chemically reactive part of the fluoroalkyl silane is nearest to the original surface of the substrate and the low energy part of the fluoroalkyl silane is farthest from the original surface of the substrate. In a further embodiment of this invention a crosslinking agent enhances the crosslinking, and, further enhances the orientation of the molecules of fluoroalkyl silane. In another further embodiment the chemical bond bonding the substrate-chemically reactive part to the original surface of the substrate is formed in the presence of a condensation catalyst operable for and capable of enhancing the chemical bond.

There is also provided by the principles of this invention a low surface-energy surface produced by treating a substrate surface with any of the above-mentioned formulations; and, removing the transport medium, or alcohol, or alcohol and the condensation catalyst, from the formulation while it is in contact with the substrate surface, thereby producing a low surface-energy surface on the substrate.

DESCRIPTION OF THE PREFERRED EMBODIMENTS

Figure 1:
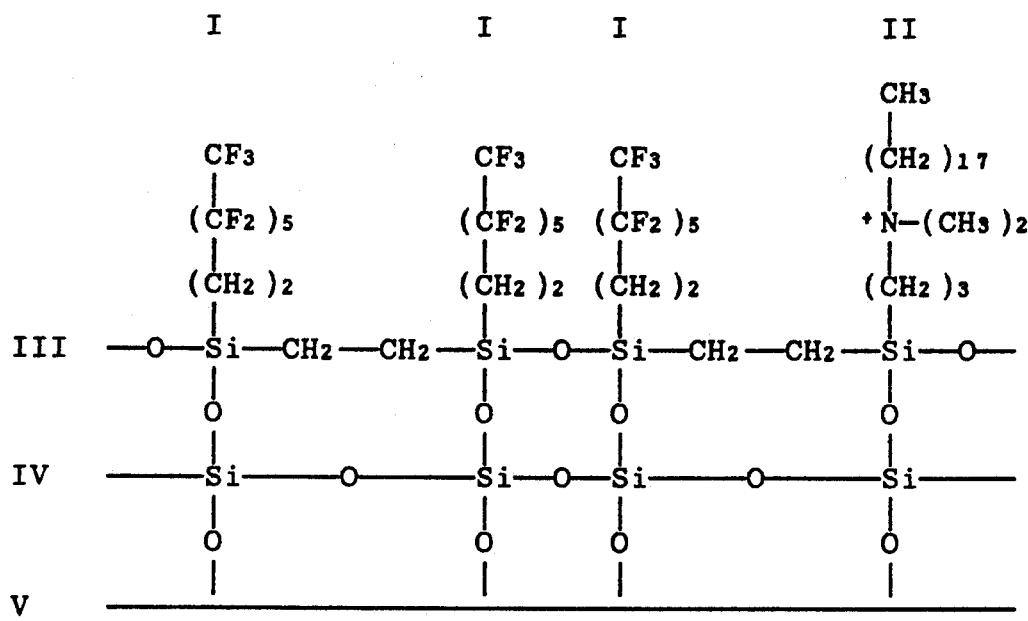
FIG. 1 is a representation of a low surface-energy surface of one embodiment of this invention.

The preferred embodiments of this invention are easily understood by reference to the following examples. All percents referred to herein are weight percents unless otherwise specified.

Borosilicate glass was used as the test substrate in the following examples. The test substrates were cleaned by washing with methanol to remove organics, dried, rinsed with dilute 0.05N hydrochloric acid to remove inorganics, rinsed with deionized water, air dried in an oven at 50° C. until dried, and, thereafter handled with cotton gloves to retain the substrates in a high state of cleanness. All solutions were flushed with dry nitrogen to prevent water absorption.

Cleaned substrate samples were dipped into the test formulations and allowed to air dry at 50% relative humidity. The surface energies of thusly treated test substrates were determined by measuring the advancing angle of water, or other suitable test liquid, on the substrate surface and converting the advancing angle to surface energy, using Young's equation, and the contact angle measurement techniques of the "tilting plate method", and the "micro-droplet method", both of which are adequately referenced in the technical literature. These measurements are easily conducted and their descriptions can be found in "PHYSICAL CHEMISTRY OF ADHESION", D. H. Kaelble, Rockwell Science Center, Wiley-Interscience, John Wiley & Sons, New York, c. 1971, page 149; "PHYSICAL CHEMISTRY OF SURFACES", A. Adamson, Wiley-Interscience, John Wiley & Sons, New York, c. 1982, page 345; and, "HANDBOOK OF PHYSICS", Condon & Odishaw, McGraw-Hill Book Co., New York, c. 1958, page 5-96.

The durability of the treated surfaces were rated by measuring the number of times that a graphite/epoxy composite material (C6000/F-155) could be released from the surface after it had been molded and cured in a vacuum laminator, i.e. after the molding and curing cycle. This is a severe test because the treated substrate is heated at 121° C. (250° F.) while in contact with the graphite/epoxy composite material under a pressure of 80 psi for a period of 3 hours. An excellent release occurs with instant separation, i.e. zero lap shear force, of the graphite/epoxy composite material from the borosilicate glass upon opening of the laminator. A good release is indicated by a lap shear values under 10 psi. A poor release is indicated by a lap shear values over 10 psi.

Durability was graded by the increase in shear lap force verses the number of repetitions of the molding cycle. Due to the severity of this test, an "excellent" or "E" grade was awarded for 6 repetitions having zero lap shear force. A grade of "good" or "G" was awarded for 4 repetitions having zero lap shear force. A grade of "fair" or "F" was awarded for 2 repetitions having zero lap shear force. A grade of "poor" or "P" was awarded for 1 repetitions having zero lap shear force. A grade of "unimproved" or "U" was awarded for graphite/epoxy composite material which would not release without fracture of the borosilicate glass. A control piece of untreated borosilicate glass did not release without fracturing. This grading scale for durability, i.e. E, G, F, P or U, is referred to in the Examples and Table 1.

EXAMPLE NO. 1

In Example No. 1 the surface energy of a cleaned test substrate sample of borosilicate glass was determined as about 47 dynes/cm at a relative humidity of 1% in air.

EXAMPLE NO. 2

Example No. 2 is the experimental results obtained by treating a sample of glass, as the substrate, with an methanol solution containing 0.8% tridecafluoro-1,1,2,2-tetrahydrooctyl-1-triethoxysilane, 0.2% n-octadecyldimethyl[3-(trimethoxysily)-propyl]ammonium chloride, 0.2% bis-1,2-(trimethoxysilyl)-ethane, and, 0.1% N,N-dimethyl benzylamine.

This formulation reacted instantly with the test substrate to produce an autophobic surface that could not be re-wetted even with its own treating formulation. The thickness was estimated by Auger Electron Spectroscopy (AES) to be between about 100 and about 200 Angstroms. The surface tension was determined to be about 11.5 dynes/cm. The durability was found to be excellent or "E".

FIG. 1 is an idealized representation of a low surface-energy surface of this invention employing tridecafluoro-1,1,2,2-tetrahydrooctyl-1-triethoxysilane as the fluoroalkyl silane, n-octadecyldimethyl[3-(trimethoxysily)-propyl]ammonium chloride as the liquid crystal silane, and, bis-1,2-(trimethoxysilyl)-ethane as the cross-linking agent. It should be understood, however, that variations from the idealized structure exist for the actual surfaces and that the molecular structure represented by FIG. 1 is merely for purposes of illustration of the principles of this invention.

EXAMPLE NO. 3

This test was the same as Example No. 2, except that the crosslinking agent, i.e. bis-1,2-(trimethoxysilyl)-ethane, was omitted from the formulation. The surface tension was determined to be about 14 dynes/cm. The durability was found to be as fair or "F".

Figure 2:
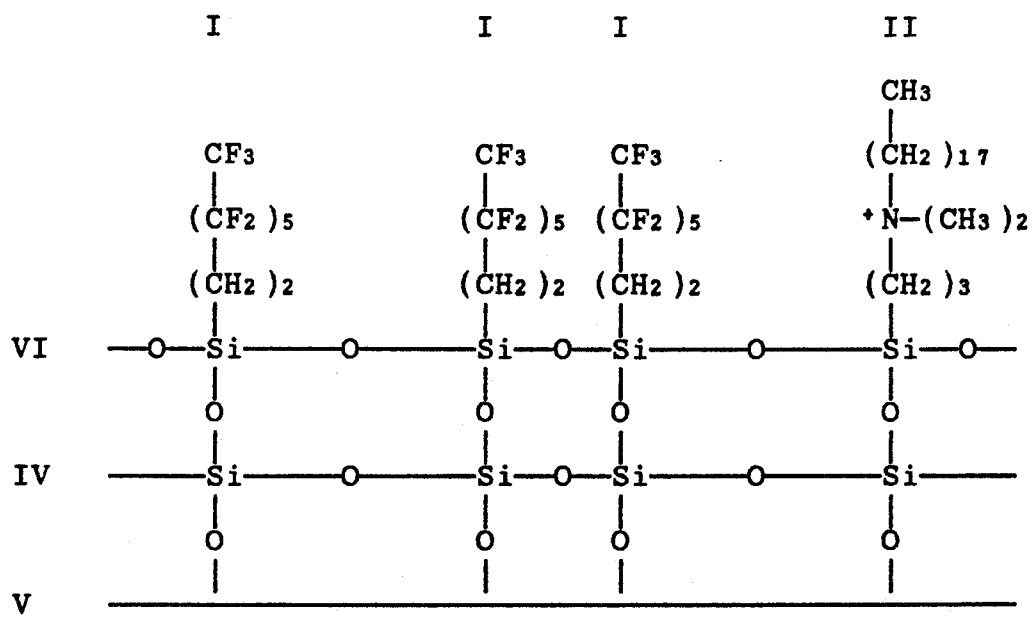
FIG. 2 is a representation of a low surface-energy surface of another embodiment of this invention.

FIG. 2 is an idealized representation of an low surface-energy surface of this invention employing tridecafluoro-1,1,2,2-tetrahydrooctyl-1-triethoxysilane as the fluoroalkyl silane, and, n-octadecyldimethyl[3-(trimethoxysily)-propyl]ammonium chloride as the liquid crystal silane. As mentioned above, the crosslinking agent, i.e. bis-1,2-(trimethoxysilyl)-ethane, was omitted from the formulation. It should also be understood that variations in this idealized structure can exist for the actual surfaces and FIG. 2 is merely for purposes of illustration.

In FIGS. 1 and 2, columns I represent low surface energy components produced from tridecafluoro-1,1,2,2-tetrahydrooctyl-1-triethoxysilane. Column II represents liquid crystals components produced from n-octadecyldimethyl[3-(trimethoxysily)-propyl]ammonium chloride. Layer III represents crosslinking produced from bis-1,2-(trimethoxysilyl)-ethane. Layer IV represents silane surface layer, the chemical bonding of which to the substrate layer V has been enhanced by the condensation catalyst N,N-dimethyl benzylamine which evaporates away upon drying. Layer VI represents crosslinking between the fluoroalkyl silane and the liquid crystal silane in the absence of a crosslinking agent.

EXAMPLE NO. 4

This test was the same as Example No. 3, except that the liquid crystal silane, i.e. n-octadecyldimethyl[3-(trimethoxysily)-propyl]ammonium chloride, was also omitted from the formulation. The surface tension was determined to be about 15 dynes/cm. The durability was found to be good or "G".

EXAMPLE NO. 5

This test was the same as Example No. 3, except that the fluoroalkyl silane, i.e. tridecafluoro-1,1,2,2-tetrahydrooctyl-1-triethoxysilane, was omitted from the formulation. The surface tension was determined to be about 28 dynes/cm. Since the glass coupons shattered before the composite released from the surface, the durability was found to be unimproved or "U".

EXAMPLE NO. 6

This test was the same as Example No. 2, except that both the fluoroalkyl silane, i.e. tridecafluoro-1,1,2,2-tetrahydrooctyl-1-triethoxysilane, and the liquid crystal silane, i.e. n-octadecyldimethyl[3-(trimethoxysily)-propyl]ammonium chloride, were omitted from the formulation. The surface tension was determined to be about 35 dynes/cm. Since the glass coupons shattered before the composite released from the surface, the durability was found to be unimproved or "U".

EXAMPLE NO. 7A

This test was the same as Example No. 4, except that the condensation catalyst, i.e. N,N-dimethyl benzylamine was omitted from the formulation. The surface tension was determined to be about 15 dynes/cm. The durability was found to be fair or "F".

EXAMPLE NO. 7B

This test was the same as Example No. 7A, except that a commercially available alkylsilane compound for forming low surface-energy surfaces was used. The surface energy was determined to be about 23 dynes/cm, and, required a large lap shear of 60 psi to effect one release. The durability was grade as less than poor or "P-".

EXAMPLE NO. 8

A glass substrate was treated with a methanol solution containing 0.8% tridecafluoro-1,1,2,2-tetrahydrooctyl-1-triethoxysilane, 0.12% n-octadecyltrimethoxysilane, 0.24% tetraethylorthosilicate, and, 0.1% N,N-dimethyl benzylamine. The formulation reacted instantly with the glass substrate to produce an autophobic surface. The surface tension was determined to be about 11.5 dynes/cm, and the durability was found to be as excellent or "E".

EXAMPLE NO. 9

A glass substrate was treated with a methanol solution containing 0.8% tridecafluoro-1,1,2,2-tetrahydrooctyl-1-triethoxysilane, 0.2% n-octadecyldimethyl[3-(trimethoxysilyl)propyl]ammonium chloride, 0.2% tetraethylorthosilicate, and, 0.1% N,N-dimethyl benzylamine. The formulation reacted instantly with the glass substrate to produce an autophobic surface. The surface tension was determined to be about 12.8 dynes/cm, and the durability was found to be excellent or "E".

EXAMPLE NO. 10

A glass substrate was treated with a methanol solution containing 0.8% tridecafluoro-1,1,2,2-tetrahydrooctyl-1-triethoxysilane, 0.11% n-methylaminopropyltrimethoxysilane, 0.22% tetraethylorthosilicate, and, 0.1% N,N-dimethyl benzylamine. The formulation reacted instantly with the glass substrate to produce an autophobic surface. The surface tension was determined to be about 11.5 dynes/cm, and the durability was found to be excellent or "E".

A condensed summary of Example Nos. 2 to 7B are shown in Table 1, where "X" means that the compound is present in the formulation.

TABLE 1

| Example No. | 2 | 3 | 4 | 5 | 6 | 7A | 7B |
|---|---|---|---|---|---|---|---|
| Fluoroalkyl silane | X | X | X | | | X | X |
| Liquid crystal silane | X | X | | X | | | |
| Crosslinking agent | X | | | | X | | |
| Condensation catalyst | X | X | X | X | X | | |
| Surface energy (dynes/cm) | 11.5 | 14 | 15 | 28 | 35 | 15 | 23 |
| Durability | E | F | G | U | U | F | P- |

The surface energy of cleaned sheet of glass was carefully measured and found it to be 47 dyne/cm, see Example No. 1. When the sheet of glass was treated with a fluoroalkyl silane and a condensation catalyst the surface energy was reduced to 15 dyne/cm, see Example No. 4.

When the sheet of glass was treated with a liquid crystal silane and a condensation catalyst the surface energy was also reduced but only to 28 dyne/cm, see Example No. 5. If one skilled in the art were to add the liquid crystal silane to the mixture of fluoroalkyl silane and condensation catalyst one would expect a surface energy somewhere between 15 and 28 dyne/cm with a surface energy nearing 15 dyne/cm as the mixture nears 100% fluoroalkyl silane and condensation catalyst and nearing 28 dyne/cm as the mixture nears 100% liquid crystal silane and condensation catalyst. However, the results demonstrate that by adding liquid crystal silane of this invention to the fluoroalkyl silane of this invention and condensation catalyst an improved result is achieved, namely the surface energy is reduced to 14 dyne/cm, see Example No. 3.

The experiments demonstrate that instead of an increasing of surface energy by the dilution of the fluoroalkyl silane with liquid crystal silane, a decreasing of surface energy occurs which is an improvement. Therefore while some of the fluoroalkyl silane molecules have been replaced with higher surface energy liquid crystal silane molecules thereby providing less low energy sites, i.e. less fluorinated parts, the fluoroalkyl silane molecules that are present were oriented by the liquid crystal silane molecules and such orientation maintained so that the fluorinated parts or low energy parts of the fluoroalkyl silane molecules are more effective thereby producing an even lower, low surface energy surface. This orientation is achieved and maintained by the crosslinking of the fluoroalkyl silane molecules with the liquid crystal silane molecules.

The fluoroalkyl silane molecules have been oriented by the liquid crystal silane molecules so that they are perpendicular to the virgin surface of the substrate and further so that their fluorinated part or low energy part is furthermost from the virgin surface of the substrate as illustrated in FIG. 2. Referring to FIG. 2, a molecular layer is formed on the virgin surface of the substrate. This molecular layer is held together and oriented by crosslinking between the fluoroalkyl silane molecules (I) and the liquid crystal silane molecules (II) as illustrated by designated crosslinked layers IV and VI of FIG. 2. As mentioned above, the thickness was estimated by AES to be between 100 and 200 Å.

Therefore the liquid crystal silane employed by this invention is required to:

(i) have the property of enhancing the orientation or alignment of the fluoroalkyl silane thereby lowering the low surface energy even lower, and (ii) to crosslink with the fluoroalkyl silane to improve stability of the oriented fluoroalkyl silane molecules.

The thusly produced low surface energy substrate surfaces of this invention resisted water, oils, greases, various other solvents, and moderate levels of abrasion such as rubbing with cloths. Such low surface-energy substrate surfaces will also resist compression molding with polymers or composite materials. Used surfaces can be retreated with the formulation to restore it nonwettable properties. The low surface-energy surfaces of this invention, however, will not endure harsh physical abrasion such as sandpaper, abrasive cleaners, strong alkalis and some mineral acids.

While the preferred embodiments of the present invention have been described, it should be understood that various changes, adaptations and modifications may be made thereto without departing from the spirit of the invention and the scope of the appended claims. It should be understood, therefore, that the invention is not to be limited to minor details of the illustrated invention shown in preferred embodiment, examples and the figures and that variations in such minor details will be apparent to one skilled in the art.

Therefore it is to be understood that the present disclosure and embodiments of this invention described herein are for purposes of illustration and example and that modifications and improvements may be made thereto without departing from the spirit of the invention or from the scope of the claims. The claims, therefore, are to be accorded a range of equivalents commensurate in scope with the advances made over the art.

INDUSTRIAL APPLICABILITY

Low surface-energy surfaces are useful for oil and water repellant surfaces, self-cleaning surfaces, mold release agents, self-cleaning surfaces, antistick surfaces, corrosion barriers, etch resistant surfaces, non-bonding surfaces, antimigration compounds and non-reacting and inert surfaces.

What is claimed is:

1. A formulation for forming a low surface-energy surface on a substrate comprising:
   a. a fluoroalkyl silane;
   b. an effective amount of a liquid crystal silane for enhancing the low surface energy property of the fluoroalkyl silane; and,
   c. a transport medium for applying the fluoroalkyl silane and the liquid crystal silane to the surface of a substrate; wherein the effective amount of liquid crystal silane in combination with the fluoroalkyl silane is operable for producing a surface energy on such low surface-energy surface that is lower than the surface energy formed from a formulation comprising the fluoroalkyl silane and the transport medium without the liquid crystal silane.

2. The formulation of claim 1, wherein the fluoroalkyl silane has the general formula

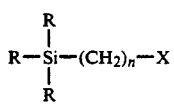

wherein "n" is at least 2, wherein at least one R is selected from the group consisting of methyl groups, ethyl groups, and mixtures thereof, wherein at least one R is selected from the group consisting of Cl, Br, $OCH_3$, and $OC_2H_5$ radicals, and mixtures thereof, which are hydrolyzable to form a silanol, and, wherein X is selected from the group consisting of fluorinated aliphatic groups, fluorinated alicyclic groups, and mixtures thereof, having a low surface energy part.

3. The formulation of claim 1, wherein the fluoroalkyl silane is tridecafluoro-1,1,2,2-tetrahydrooctyl-1-triethoxysilane.

4. The formulation of claim 1, wherein the liquid crystal silane is n-octadecyldimethyl[3-(trimethoxysily)-propyl] ammonium chloride.

5. The formulation of claim 1, further comprising a crosslinking agent for crosslinking the fluoroalkyl silane.

6. The formulation of claim 5, wherein the crosslinking agent is selected from the group consisting of multifunctional silyl ethers, multifunctional silicates, and mixtures thereof, which are capable of hydrolysis and reaction with the fluoroalkyl silane and the liquid crystal silane.

7. The formulation of claim 1, further comprising a condensation catalyst for enhancing chemical bonding of the fluoroalkyl silane to the substrate.

8. The formulation of claim 1, wherein the transport medium is an alcohol.

9. The formulation of claim 8, wherein the alcohol is selected from the group consisting of methanol, ethanol, and mixtures thereof.

10. The formulation of claim 1, wherein the formulation is operable for producing an autophobic surface having a thickness as determined by Auger Electron Spectroscopy of between about 100 and about 200 Å.

11. A formulation for forming a low surface-energy surface on a substrate comprising:
    a. a fluoroalkyl silane having the general formula

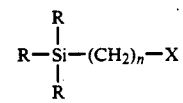

wherein "n" is at least 2, wherein at least one R is selected from the group consisting of alkyl groups, wherein at least one R is selected from the group consisting of halogens, alkyl ethers, and mixtures thereof, which are hydrolyzable to form a silanol, and, wherein X is selected from the group consisting of fluorinated aliphatic groups, fluorinated alicyclic groups, and mixtures thereof, having a low surface energy part;

b. an effective amount of a liquid crystal silane for enhancing the low surface energy property of the fluoroalkyl silane; and,
   c. a transport medium for applying the fluoroalkyl silane and the liquid crystal silane to the surface of a substrate; wherein the effective amount of liquid crystal silane in combination with the fluoroalkyl silane is operable for producing a surface energy on such low surface-energy surface that is lower than the surface energy formed from a formulation comprising the fluoroalkyl silane and the transport medium without the liquid crystal silane.

12. The formulation of claim 11, wherein X is completely fluorinated.

13. The formulation of claim 11, wherein X is partially fluorinated.

14. The formulation of claim 11, wherein the formulation is operable for producing a surface having a thickness of between about 100 and about 200 Å.

15. A formulation for forming a low surface-energy surface on a substrate comprising:

a. A fluoroalkyl silane having the general formula

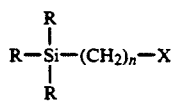

wherein "n" is at least 2,
wherein one of the R's is selected from the group consisting of alkyl groups,
wherein two of the R's are selected from the group consisting of halogens, alkyl ethers, and mixtures thereof, which are hydrolyzable to form a silanol, and,
wherein X is selected from the group consisting of fluorinated aliphatic groups, fluorinated alicyclic groups, and mixtures thereof, having a low surface energy part;

b. an effective amount of a liquid crystal silane for enhancing the low surface energy property of the fluoroalkyl silane; and, c. a transport medium for applying the fluoroalkyl silane and the liquid crystal silane to the surface of a substrate; wherein the effective amount of liquid crystal silane in combination with the fluoroalkyl silane is operable for producing a surface energy on such low surface-energy surface that is lower than the surface energy formed from a formulation comprising the fluoroalkyl silane and the transport medium without the liquid crystal silane.

16. The formulation of claim 15, wherein the formulation is operable for producing a surface having a thickness of between about 100 and about 200 Å.

17. A formulation for forming a low surface-energy surface on a substrate comprising:

a. a fluoroalkyl silane:
b. an effective amount of a liquid crystal silane having the general formula

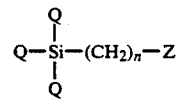

wherein n is at least 2,
wherein Q is selected from the group consisting of halogens, alkyl ethers, and mixtures thereof, which are hydrolyzable to form a silanol, and,
wherein Z is selected from the group consisting of organic groups having liquid crystal properties, for enhancing the low surface energy property of the fluoroalkyl silane; and, c. a transport medium for applying the fluoroalkyl silane and the liquid crystal silane to the surface of a substrate; wherein the effective amount of liquid crystal silane in combination with the fluoroalkyl silane is operable for producing a surface energy on such low surface-energy surface that is lower than the surface energy formed from a formulation comprising the fluoroalkyl silane and the transport medium without the liquid crystal silane.

18. The formulation of claim 17, wherein the Z is selected from the group consisting of alkyl quaternary ammonium salts, substituted biphenyl compounds, terphenyl compounds, azoxybenezenes, cinnamates, pyrimidines, benzoates, and mixtures thereof.

19. The formulation of claim 17, wherein the formulation is operable for producing a surface having a thickness, of between about 100 and about 200 Å.

20. A formulation for forming a low surface-energy surface on a substrate comprising:

a. a fluoroalkyl silane:
b. an effective amount of a liquid crystal silane having the general formula

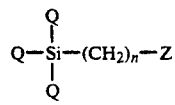

wherein n is at least 2, wherein Q is selected from the group consisting of Cl, Br, $OCH_3$, $OC_2H_5$ radicals, and mixtures thereof, which are hydrolyzable to form a silanol, and, wherein Z is selected from the group consisting of organic groups having liquid crystal properties, for enhancing the low surface energy property of the fluoroalkyl silane; and, c. a transport medium for applying the fluoroalkyl silane and the liquid crystal silane to the surface of a substrate; wherein the effective amount of liquid crystal silane in combination with the fluoroalkyl silane is operable for producing a surface energy on such low surface-energy surface that is lower than the surface energy formed from a formulation comprising the fluoroalkyl silane and the transport medium without the liquid crystal silane.

21. The formulation of claim 20, wherein the formulation is operable for producing a surface having a thickness of between about 100 and about 200 Å.

22. A formulation for forming a low surface-energy surface on a substrate comprising:

a. a fluoroalkyl silane;
b. a liquid crystal silane for enhancing the orientation of the molecules of the fluoroalkyl silane;
c. a transport medium for applying the fluoroalkyl silane and the liquid crystal silane to the surface of a substrate; and,
d. a crosslinking agent for crosslinking the fluoroalkyl silane, wherein the crosslinking agent is selected from the group consisting of tetramethyl orthosilicates, tetraethyl orthosilicates, and mixtures thereof.

23. The formulation of claim 22, wherein the crosslinking agent is bis-1,2-(trimethoxysilyl)ethane.

24. A formulation for forming a low surface-energy surface on a substrate comprising:

a. a fluoroalkyl silane;
b. a liquid crystal silane for enhancing the orientation of the molecules of the fluoroalkyl silane;
c. a transport medium for applying the fluoroalkyl silane and the liquid crystal silane to the surface of a substrate; and,
d. a condensation catalyst for enhancing chemical bonding of the fluoroalkyl silane to the substrate, wherein the condensation catalyst is selected from the group consisting of tertiary amines, hindered secondary amines, and mixtures thereof, which are capable of catalyzing the hydrolysis and condensation of the fluoroalkyl silane and the liquid crystal silane.

25. The formulation of claim 24, wherein the condensation catalyst is N,N-dimethyl benzylamine.

26. A formulation for forming an improved low surface-energy surface on a substrate comprising:
   a. an alcohol;
   b. a fluoroalkyl silane having a low surface energy part;
   c. an effective amount of a liquid crystal silane operable
      for enhancing the low surface energy property of the fluoroalkyl silane, and
      for crosslinking with the fluoroalkyl silane;
   d. a crosslinking agent for crosslinking the fluoroalkyl silane; and,
   e. a condensation catalyst for chemically bonding of the fluoroalkyl silane to the substrate; wherein the effective amount of liquid crystal silane in combination with the fluoroalkyl silane is operable for producing a surface energy on such low surface-energy surface that is lower than the surface energy formed from a formulation comprising the fluoroalkyl silane and the transport medium without the liquid crystal silane.

27. The formulation of claim 26, wherein the fluoroalkyl silane, the liquid crystal silane, the crosslinking agent and the condensation catalyst are dissolved in the alcohol.

28. The formulation of claim 26, wherein the amount of fluoroalkyl silane is from about 0.4 to about 10% by weight of the formulation,
   wherein the amount of liquid crystal silane is from about 0.1 to about 5% by weight of the formulation,
   wherein the amount of crosslinking agent is from about 0.1 to about 5% of the formulation, and,
   wherein the amount of condensation catalyst is from about 0.05 to about 1% by weight of the formulation.

29. The formulation of claim 26, wherein the weight ratio of the liquid crystal silane to the fluoroalkyl silane is from about 0.05 to about 0.5,
   wherein the weight ratio of the crosslinking agent to the fluoroalkyl silane is from about 0.05 to about 0.5, and,
   wherein the weight ratio of the condensation catalyst to the fluoroalkyl silane is from about 0.05 to about 0.25.

30. A formulation for treating a substrate surface to transform it into a low surface-energy surface, the formulation comprising:
   a. an alcohol;
   b. an effective amount of a fluoroalkyl silane operable for forming a low surface-energy substrate surface, the molecules of the fluoroalkyl silane having a low energy part and a substrate-chemically reactive part;
   c. an effective amount of a liquid crystal silane operable
      for enhancing the low surface energy property of the fluoroalkyl silane so that the low energy part thereof forms a surface on the substrate having a lower surface energy than such surface would have in the absence of the liquid crystal silane, and
      for crosslinking with the fluoroalkyl silane;
   d. an effective amount of a crosslinking agent for crosslinking and orienting molecules of the fluoroalkyl silane so that the low energy part thereof forms a surface on the substrate having a lower surface energy than such surface would have in the absence of the crosslinking agent; and,
   e. an effective amount of a condensation catalyst for enhancing the reaction of the substrate-chemically reactive part of the fluoroalkyl silane to the substrate surface so that the durability of the low surface-energy surface on the substrate is greater than the durability of such low surface-energy surface formed in the absence of the condensation catalyst; wherein the effective amount of liquid crystal silane in combination with the fluoroalkyl silane is operable for producing a surface energy on such low surface-energy surface that is lower than the surface energy formed from a formulation comprising the fluoroalkyl silane and the transport medium without the liquid crystal silane.

* * * * *